(12) United States Patent
Trainoff

(10) Patent No.: US 9,658,194 B2
(45) Date of Patent: May 23, 2017

(54) CONTROLLING INTERDETECTOR BAND BROADENING

(71) Applicant: Wyatt Technology Corporation, Santa Barbara, CA (US)

(72) Inventor: Steven P. Trainoff, Goleta, CA (US)

(73) Assignee: WYATT TECHNOLOGY CORPORATION, Goleta, CA (US)

( * ) Notice: Subject to any disclaimer, the term of this patent is extended or adjusted under 35 U.S.C. 154(b) by 112 days.

(21) Appl. No.: 14/378,515

(22) PCT Filed: Feb. 7, 2013

(86) PCT No.: PCT/US2013/025217
§ 371 (c)(1),
(2) Date: Aug. 13, 2014

(87) PCT Pub. No.: WO2013/122817
PCT Pub. Date: Aug. 22, 2013

(65) Prior Publication Data
US 2015/0027203 A1  Jan. 29, 2015

Related U.S. Application Data

(60) Provisional application No. 61/598,841, filed on Feb. 14, 2012.

(51) Int. Cl.
| | | |
|---|---|---|
| *G01N 30/02* | (2006.01) | |
| *G01N 21/41* | (2006.01) | |
| *G01N 21/47* | (2006.01) | |
| *G01N 21/49* | (2006.01) | |
| *G01N 30/16* | (2006.01) | |
| *H01J 49/04* | (2006.01) | |
| *G01N 30/78* | (2006.01) | |
| *G01N 30/84* | (2006.01) | |

(52) U.S. Cl.
CPC ............ *G01N 30/02* (2013.01); *G01N 21/41* (2013.01); *G01N 21/4133* (2013.01); *G01N 21/47* (2013.01); *G01N 21/49* (2013.01); *G01N 30/16* (2013.01); *G01N 30/78* (2013.01); *G01N 30/84* (2013.01); *H01J 49/0431* (2013.01); *G01N 2030/8441* (2013.01)

(58) Field of Classification Search
CPC ......... G01N 30/02; G01N 30/78; G01N 30/84
USPC .................... 73/23.4, 23.41, 61.55
See application file for complete search history.

(56) References Cited

U.S. PATENT DOCUMENTS 4,454,043 A * 6/1984 Ting ..................... G01N 30/461
210/198.2
5,089,126 A * 2/1992 Silebi ..................... B01D 43/00
209/1
(Continued)

FOREIGN PATENT DOCUMENTS

EP    2096426 A2    9/2009

*Primary Examiner* — Natalie Huls
(74) *Attorney, Agent, or Firm* — David N. Villalpando

(57) ABSTRACT

Methods and apparatus for controlling interdetector band broadening during the analysis of a sample injected into a chromatography system. A column flow is diluted with a dilution flow after the sample exits the chromatography system, and the diluted sample is analyzed by one or a combination of analysis instruments such as a light scattering detector, refractive index detector, an ultraviolet absorption detector.

14 Claims, 8 Drawing Sheets

(56) References Cited

U.S. PATENT DOCUMENTS

| | | | | |
|---|---|---|---|---|
| 5,129,723 A | * | 7/1992 | Howie | G01N 21/51 356/336 |
| 5,449,902 A | * | 9/1995 | Onishi | G01N 30/728 250/281 |
| 6,294,388 B1 | | 9/2001 | Petro | |
| 6,411,383 B1 | * | 6/2002 | Wyatt | G01N 21/47 250/574 |
| 6,651,009 B1 | * | 11/2003 | Trainoff | G01N 15/06 250/574 |
| 8,621,915 B2 | * | 1/2014 | Liu | G01N 30/463 210/656 |
| 2005/0075851 A1 | * | 4/2005 | Trainoff | G01N 30/8624 703/9 |
| 2008/0201111 A1 | | 8/2008 | Trainoff | |
| 2010/0000301 A1 | * | 1/2010 | Iwata | G01N 30/463 73/61.55 |
| 2010/0107742 A1 | * | 5/2010 | Liu | G01N 30/34 73/61.56 |
| 2012/0058568 A1 | | 3/2012 | Sasaki et al. | |

\* cited by examiner

CONTROLLING INTERDETECTOR BAND BROADENING

TECHNICAL FIELD

The present disclosure relates generally to chromatographic methods and apparatus for chemical analysis. The present disclosure also relates to controlling inter-detector band broadening in a chromatography system to provide more accurate comparison of measurements of a sample by a chain of analytical instruments.

BACKGROUND

Macromolecular characterization of liquid chromatography consists of analyzing the fractionated sample that elutes from a chromatography column with serially connected detectors that each measure different properties of the sample. A typical detector chain that can be used to measure the molar mass and radius of gyration consists of a multi-angle light scattering detector (MALS) and a refractive index detector. There are many other detectors that can also be added to the analysis chain, including but not limited to, UV absorption, differential viscometry, quasi-elastic light scattering, and mass spectrometry. However in the process of flowing between detectors the sample, fractionated by the columns, becomes increasingly remixed as the sample is sheared in the tubing and mixed by passage through the various measurement cells. This is the problem of inter-detector band broadening which is distinct from the related problem of mixing and broadening within the chromatography columns, which is typically referred to as column broadening.

In order to extract physical parameters one must often compare the signal from different detectors for the same physical aliquot of sample as it passes through the analysis chain. However since the sample is being slowly remixed there are two effects that will affect this comparison. The first is that a peak of uniform composition, but varying concentration, will be affected by having the peak shape broaden. In general the first detector will measure the narrowest peak, which will be subsequently increased as the sample progresses through the detector chain. For example, in light scattering analysis, the molecular weight of the sample at low concentration is proportional to the ratio of the light scattering signal $$M(t) \propto LS(t)/RI(t). \qquad (1)$$

where M(t) is the molar mass of the sample as a function of time, LS(t) is the light scattering signal as a function of time, and RI/(t) is the differential refractive index detector as a function of time. Consider what happens if a monodisperse sample is measured by an analysis chain that consists of light scattering instrument followed by a refractive index detector. Since the sample is monodisperse, the molar mass across the peak is constant so that in this case M(t)=M and we find that the two detector responses should be directly proportional to each other $LS(t) \propto RI(t)$. This means if we measure a peak and scale them to the sample amplitude, they should overlay perfectly. However, in the case that there is inter-detector band broadening, the peak shape of the downstream detector, being broadened, is no longer directly proportional to the upstream detector and we find that the RI peak is broader than the LS peak. When the molecular weight analysis is performed, this leads to an error in the derived molar mass. In the literature, there have been various methods proposed for addressing this problem that consists of modeling the mixing that occurs, for example, see U.S. Pat. No. 7,386,427 by Trainoff, "Method for correcting the effects of interdetector band broadening," and applying mathematical corrections the compensate for the change in peak shape. These methods work well as long as the broadening is small compared to the peak width. A rough rule of thumb is that if the broadening increases the peak width by 20% or less, the numerical corrections can correct for the effect.

The second effect of broadening, is to mix two adjacent peaks of different composition. This is equivalent to a loss of resolution. This is a more difficult problem because numerical modeling typically assumes that the sample that passes through each detector is well fractionated and that at any given time the sample in each detector is nearly monodisperse. When the inter-detector broadening makes the sample polydisperse, it is much more difficult to correct numerically.

A trend in liquid chromatography is towards narrower bore columns that shorten run times and increase resolution. A typical standard bore chromatography column has an internal diameter of 4-5 mm and requires a solvent flow rate of around 1 ml/min for optimal resolution. When a sample is injected into such a system the individual components are fractionated into a series of peaks that each have an eluted volume of around 1 ml. In order to avoid excessive inter-detector broadening the analysis instruments are designed to have as low an internal volume as is possible. However even if the internal volume of the cell is small, the effective mixing volume may be larger than the physical volume depending on the flow characteristics of the cell. For example the Optilab® T-rEX™ differential refractive index cell manufactured by Wyatt Technology has an internal volume of 7.5 µl, but the triangular shape of the cell makes it difficult to flush the corners which results in an effective mixing volume of around 15 µl for a flow rate of 1.0 ml/min when there is turbulent mixing in the cell, and as much as 200 µl for a flow rate of 0.1 ml/min, which results in laminar flow in the cell that does not adequately flush the corners. In general, the effective mixing volume is closer to the physical volume for higher flow rates.

The total inter-detector broadening is a combination of the mixing that occurs as the sample exits the first cell, travels through the capillary tubing to the second instrument and then is mixed entering the second cell. For the example of a Wyatt Technology DAWN® HELEOS® multi-angle light scattering (MALS) instrument followed by an Optilab T-rEX DRI system, the effective inter-detector broadening for a flow rate of 1.0 ml/min is roughly 50 µl, which is only 5% of the typical peak width of 1.0 µl. This is well less than the 20% rule of thumb mentioned earlier and the numerical band broadening correction works well. However for a narrow bore chromatography column such as the Waters Acquity column that has an internal diameter of 3.0 mm and a flow rate of 0.3 ml/min, the peak widths drop by roughly a factor of 10 to approximately 100 µl. In this case, the inter-detector broadening actually increases somewhat due to the lower flow rate, but even at 50 µl mixing volume it represents 50% of the peak width and the numerical broadening corrections perform poorly. The peaks are highly distorted and the there is substantial loss of resolution. Clearly there is a strong incentive to make the effective broadening volume as small as possible, but at some point instrumental design and manufacturing considerations limit how small an experimental cell can be. It is the subject of this invention to present a method of controlling the effects of inter-detector band broadening.

BRIEF DESCRIPTION OF THE DRAWINGS

Understanding that drawings depict only typical embodiments of the invention and are not therefore to be considered to be limiting of its scope, the invention will be described and explained with specificity and detail through the use of the accompanying drawings as listed below.

DETAILED DESCRIPTION OF THE INVENTION

It will be readily understood that the components of the embodiments as generally described and illustrated in the figures herein could be arranged and designed in a wide variety of different configurations. Thus, the following more detailed description of various embodiments, as represented in the figures, is not intended to limit the scope of the invention, as claimed, but is merely representative of various embodiments. While the various aspects of the embodiments are presented in drawings, the drawings are not necessarily drawn to scale unless specifically indicated.

Figure 1:
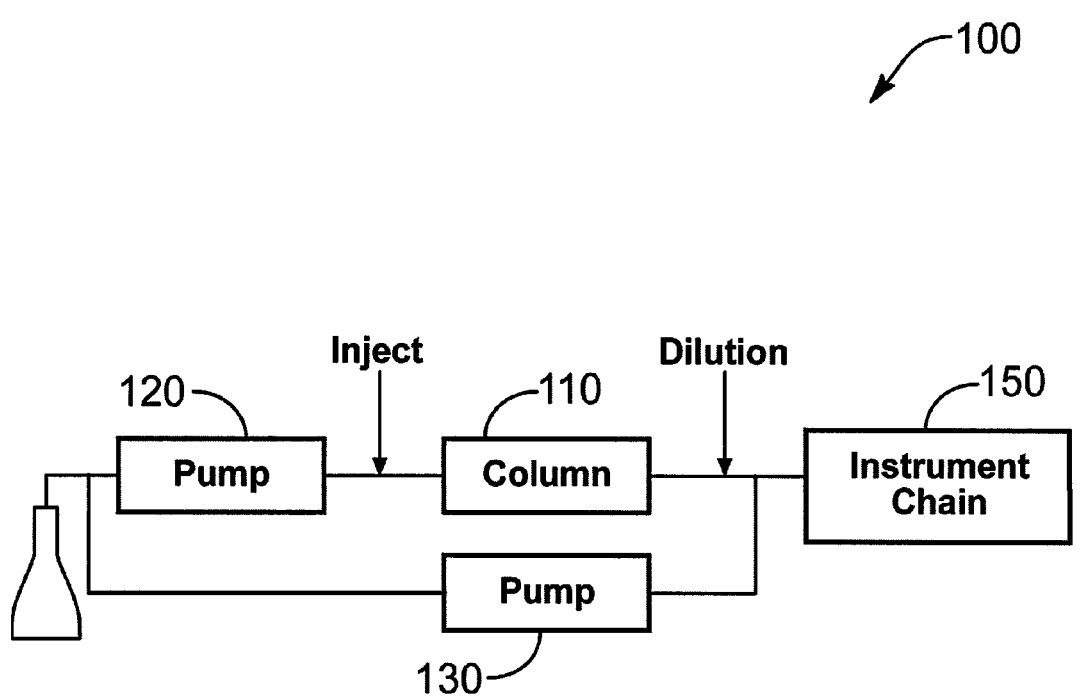
FIG. 1 is a block diagram of a sample analysis system.

Chromatographic systems, such as those used in the basic sample analysis system 100 shown in FIG. 1, may be used to separate a sample into various components so that these components can be identified and quantified. Chromatographic techniques can be applied to gaseous samples as well as to liquid samples including chemical, biological and medical samples.

A variety of mechanisms are utilized to produce the desired separation between the components of the sample. In one example, the wall of a capillary tube or column through which a sample flows, such as fractionation column 110 shown in FIG. 1, may be used to separate the sample components based on size and/or chemical affinity. The sample can be forced through this matrix by a number of techniques, such as a pressure difference created between the inlet and outlet ends of the capillary or column. Such a pressure difference may be created by a pump, such as pump 120 and/or pump 130 shown in FIG. 1.

After separation of the sample by a chromatographic system, a capillary tube may transfer the sample solution to one or more detection instruments that measure some physical property of the components, such as, but not limited to, light scattering, mass spectroscopy, the absorbance spectrum, the fluorescence spectrum, the refractive index, the nuclear magnetic resonance, or the electrical conductivity of the sample solution. In the example shown by FIG. 1, a capillary tube may transfer the separated sample to the instrument chain 150 including one or more detection instruments, such as a light scattering (LS) detector and a refractive index (RI) detector which may be connected in series after the fractionation column 110.

In one example, the LS and RI concentration signals may be produced by two different instruments in the instrument chain 150 separated by a short length of tubing. To drive corresponding measurements, the instruments in the instrument chain should analyze the same portion of the fractioned sample as it flows through the tubing. In other words, the instruments should make their analysis on the same "slice" of the sample as it moves through the tubing. This means there will be a time delay between corresponding slices that must be determined for accurate analysis. In addition, the connecting tubing as well as the flow cells of the two instruments may create some mixing of the sample that tends to degrade the sample separation/fractionation performed by the chromatographic system. As such, a short section of flow does not remain unchanged as it travels through the system, but mixes somewhat with other slices during its passage from one detector to the next. The contamination of a slice with sample fractions from other slices as it travels from one detector to another will create errors in the computed results, such as the molecular weight distribution. The tubing distance and mixing of the sample has the effect of broadening the detection peaks as the sample is analyzed by the instrument chain. This effect is called interdetector band broadening. The effect of interdetector band broadening should be kept small to minimize measurement errors during the analysis of fractionated samples.

As shown in the following examples, the interdetector band broadening may be minimized by increasing the flow through the chain of analysis instruments by diluting the sample with an auxiliary dilution flow.

Example 1

In order to highlight the effect of interdetector broadening and the associated loss of resolution, an experimental system 200 was set up to mimic the narrow peaks produced from a microbore chromatography column. This test consisted of injecting straight from an autoinjector directly to the instrument analysis chain through an inline 0.1 μm filter. This arrangement provided the opportunity to create extremely narrow peaks without the complication of developing a chromatography method.

Figure 2:
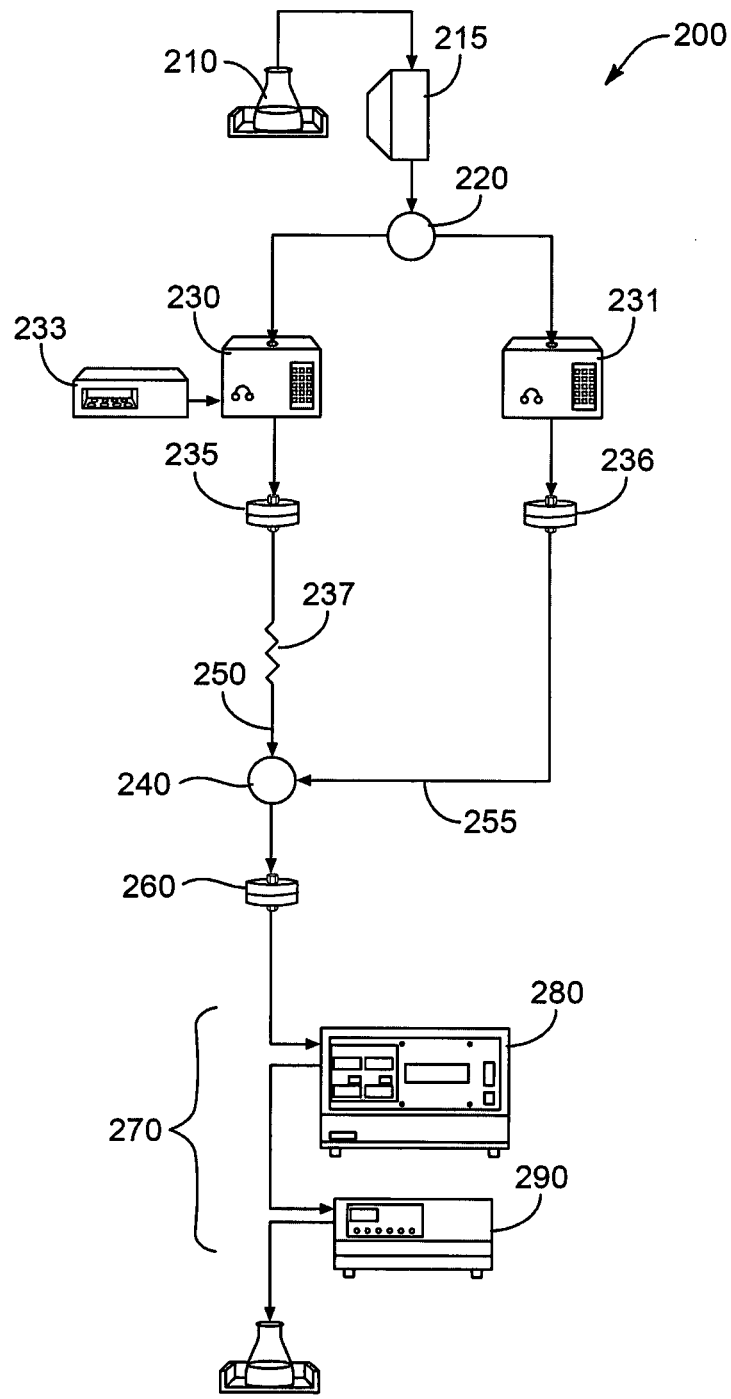
FIG. 2 is a block diagram of another sample analysis system.

As shown by FIG. 2, the experimental system 200 includes a solvent reservoir 210 used as the source for both column flow pump 230 and dilution flow pump 231. The fluid from the solvent reservoir 210 passed through an inline degasser 215. A "T" connection 220 after the degasser 215 supplied the low pressure port of both column flow pump 230 and dilution flow pump 231. Both column flow pump 230 and dilution flow pump 231 had 0.02 μm inline filters 235 and 236 on their down-stream high pressure ports. The column flow pump 230 and dilution flow pump 231 were Agilent Technologies model 1100 chromatography pumps (www.chem.agilent.com). Column flow pump 230 was used to provide the column flow 250. Dilution flow pump 231 was used to provide the dilution flow 255. The column pump 230 pressurized the column flow 250 and was plumbed to an autosampler 233 (such as the Agilent Technologies model 1100 autosampler). A 1 m length of 0.125 mm ID capillary tubing 237 was used to simulate a chromatography column within the column flow 250. By using the piece of capillary tubing 237, it is possible to eliminate the diffusive broadening of a chromatography column and make extremely narrow peaks (compared to those produced by traditional chromatography) to measure the effect of peak broadening. The capillary tubing 237 was connected to a tee union 240 to combine the column flow 250 with the dilution pump flow 255. After the exit of the tee union 240 was a 0.1 um filter 260 which served to filter the sample and fully mix the column flow 250 with the dilution pump flow 255. The solvent used was phosphate buffer (PBS) consisting of 25 mM monobasic sodium phosphate+25 mM dibasic sodium phosphate+50 mM sodium chloride+200 ppm sodium azide. The sample was 1.0 mg/ml Ovalbumen in PBS.

For purposes of example only, and not as a limitation, the instrument analysis chain 270 included a HELEOS light scattering detector 280 (DAWN HELEOS available from Wyatt Technology Corp., Santa Barbara, Calif.), followed by an Optilab rEX refractive index concentration detector 290 (Optilab rEX RI available from Wyatt Technology Corp., Santa Barbara, Calif.). The experiments were performed with a constant flow through the instrument analysis chain 270. Only the ratio of the column flow mixed with the dilution flow was changed.

The effect of interdetector band broadening is most pronounced when the peak volumes are small compared to the flow cell mixing volumes. Therefore, one goal of the experiment was to make the injection peak as narrow as possible. By eliminating the chromatography column, which itself broadens the peaks, the peak width is limited only by mixing in the injector, tubing, and flow cells. The protocol consisted of making a series of 10 µl injections of the Ovalbumen protein sample and measuring the light scattering and RI detector responses with different dilutions. Since there is no chromatographic column in the experimental system 200, the samples are not fractionated. For the low concentration samples used in this experiment, the responses from both the light scattering detector 280 and the refractive index detector 290 should be directly proportional to the concentration of the sample. Therefore, the responses of the two detectors should be directly proportional to each other. Any deviation can, therefore, be attributed to the effects of interdetector band broadening. The data is then normalized to unit amplitude so that they can be easily compared. To keep the effect of mixing in the flow cells constant, the flow rate was held at 1.0 ml/min. The ratio of the column flow 250 to the dilution flow 255 was varied from no dilution flow to a dilution ratio of 1:8. The dilutions used are shown in Table 1.

TABLE 1

| Dilution ratio | Column Flow (ml/min) | Dilution Flow (ml/min) |
|---|---|---|
| 1 | 1.0 | 0.0 |
| 2 | 0.5 | 0.5 |
| 4 | 0.25 | 0.75 |
| 8 | 0.125 | 0.875 |

Figure 3:
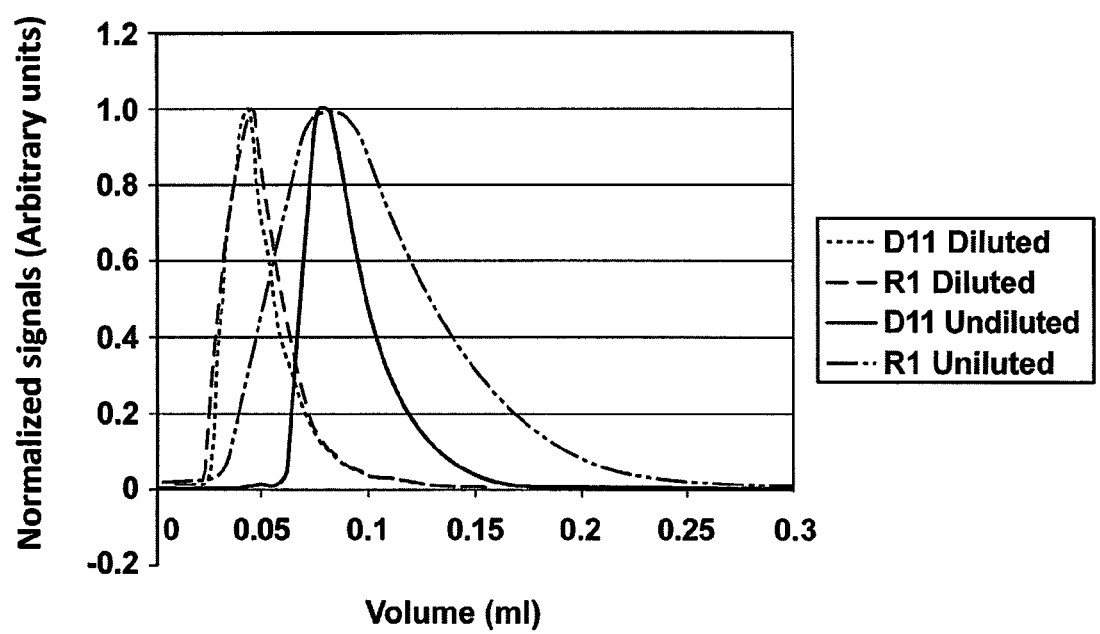
FIG. 3 is a graph comparing light scattering and refractive index data of an undiluted injection with a 1:8 dilution injection.

FIG. 3 shows the effects of diluting the sample on band broadening. The rightmost peaks are the normalized values of the 90° light scattering (LS) signal and the refractive index (RI) signal for the undiluted injection. The x axis is the volume of fluid that has passed through the column in units of ml. The leftmost peaks are the same for the 1:8 dilution. Because the test sample is unfractionated, the normalized LS and RI signals should overlay perfectly, but instead they show extreme interdetector band broadening. The diluted peaks on the left still show slight interdetector band broadening, but it has been dramatically reduced.

Figure 4:
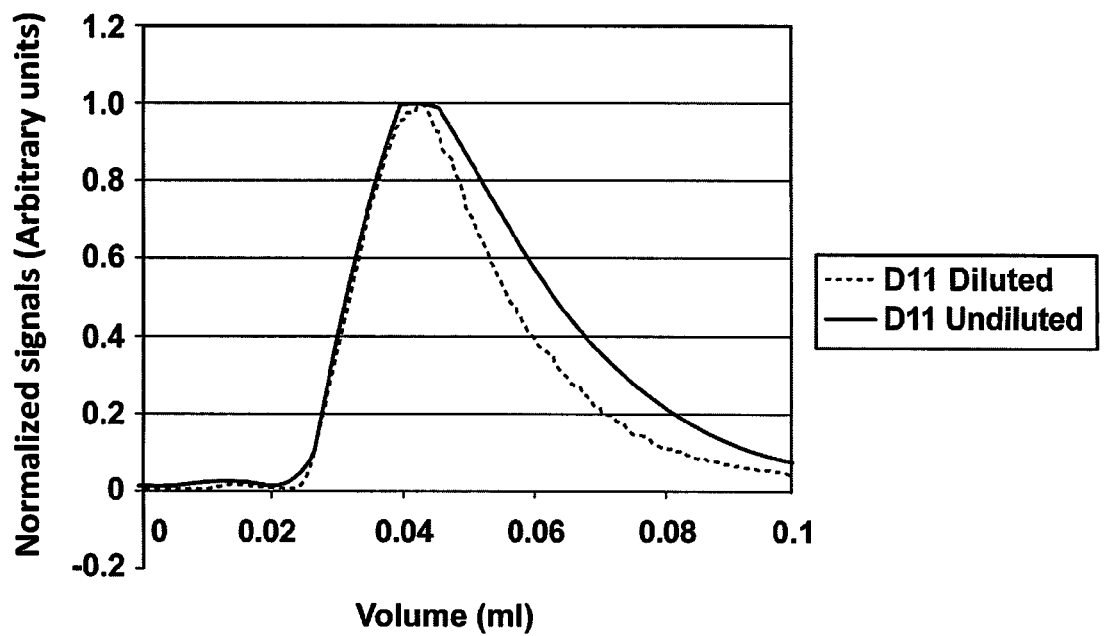
FIG. 4 is a graph comparing light scattering data peaks from the undiluted injection and the 1:8 dilution of FIG. 3.

FIG. 4 shows the same LS signal data as FIG. 3, but the curves have been shifted in time to make them overlap. The diluted peak is narrower than the undiluted peak. This demonstrates that, in addition to decreasing the interdetector broadening, an increase in the resolution of the peaks entering the analysis chain is provided by the dilution. Therefore, dilution of the sample improves resolution even if only a single detector is used.

There is no requirement that the dilution flow be the same composition as the column flow. There are applications in which it may be desirable to use a dilution solvent which differs from the column solvent. For example, an expensive or hazardous solvent might be required by the chromatography, whereas an inexpensive or non-hazardous solvent might be used by the dilution flow. Another example is reverse phase chromatography, which uses a gradient of solvent composition to separate samples. One gradient may be applied to the column and an inverse gradient may be applied to the dilution pump, so that the flow through the analysis chain will have a constant composition. This would eliminate, or dramatically reduce, the sloping baselines that are commonly seen in RI and UV detectors.

Example 2

Figure 5:
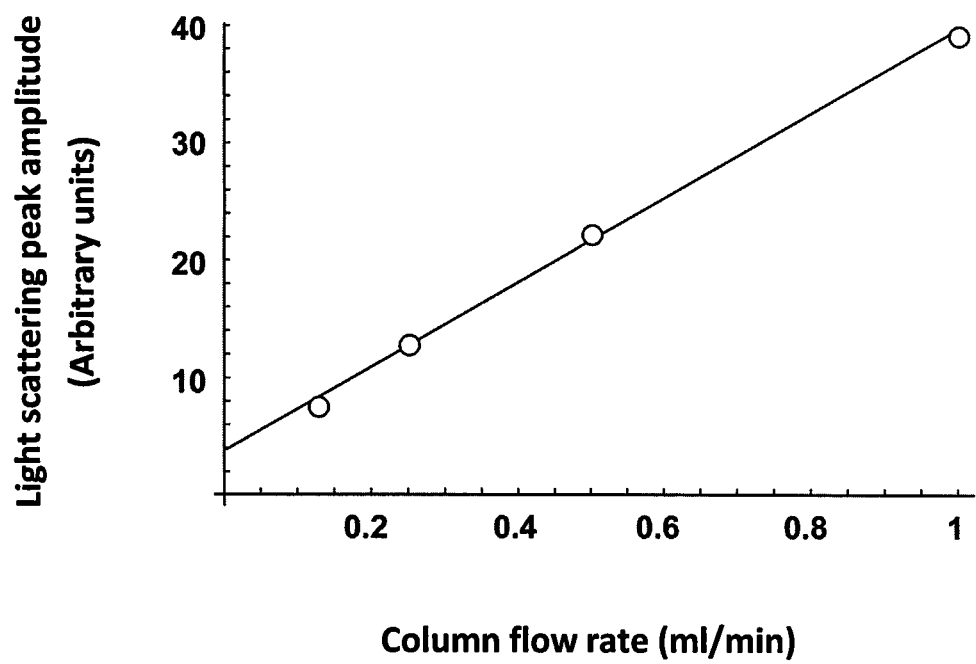
FIG. 5 is a graph plotting light scattering peak amplitude in relation to the column flow rate.

FIG. 5 shows the maximum amplitude of the LS peaks (y axis is in arbitrary units) as measured for each of the injections shown in Table 1, plotted against the column flow rate (x axis is in units of ml/min). This measures the decrease in signal to noise ratio caused by the dilution. The lower the column flow is, the higher the dilution. Therefore, the left side of the flow rate axis represents higher dilution. As expected, is it approximately linear, but it does not extrapolate to 0. The diluted peaks have larger maximum amplitudes than simply taking an undiluted peak and dividing by the dilution factor. The reason for this is that the peak areas are conserved, but the diluted peaks are narrower.

Figure 6:
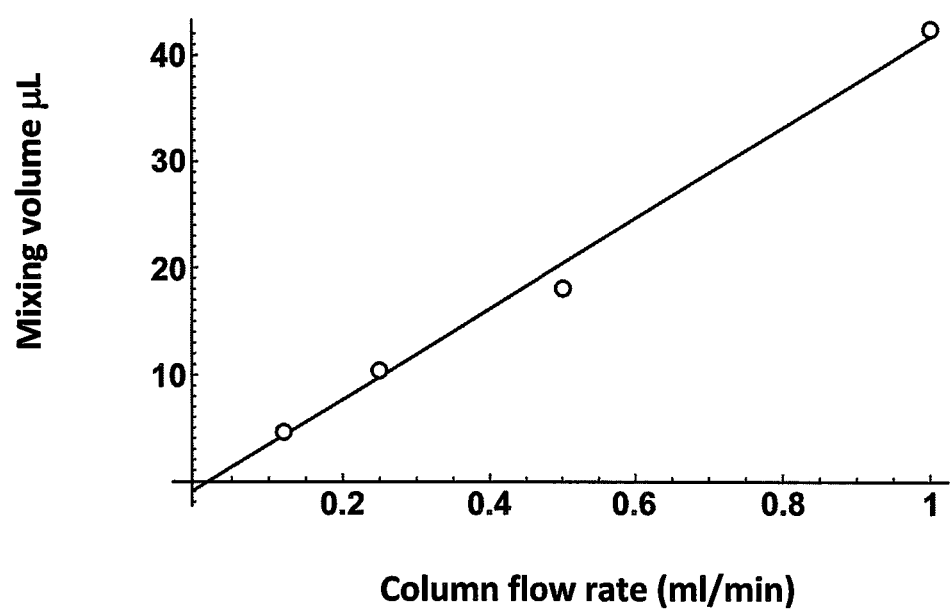
FIG. 6 is a graph plotting mixing volume in relation to flow rate.

The next analysis was to compute the change in the effective interdetector mixing volume (as described in U.S. Pat. No. 7,386,427 incorporated herein by reference). FIG. 6 shows the interdetector mixing volume, as measured in terms of the volume of fluid which passed through the column flow. Plotted on the y axis is this mixing volume in units of µl. The x axis shows the column flow rate in units of ml/min. This demonstrates that the mixing volume is directly proportional to the column flow rate (inversely proportional to the dilution factor). It also shows that the effective mixing volume can be made arbitrarily small by increasing the dilution factor. However, the tradeoff is that the more the sample is diluted, the lower the signal amplitudes become, and hence the lowering of the signal-to-noise ratio of the measured signals.

Figure 7:
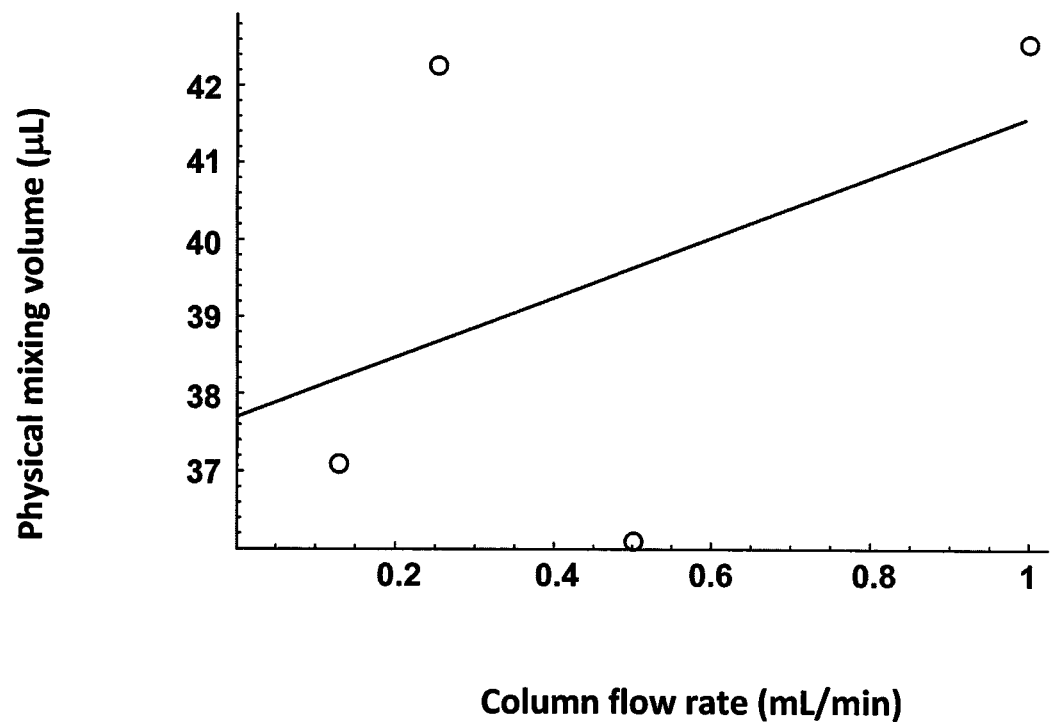
FIG. 7 is a graph plotting the physical mixing volume in relation to the column flow rate.

FIG. 7 shows the same data as FIG. 6 but presented in terms of the physical flow rate through the analysis chain, as opposed to the flow rate through the column. Since the physical volumes of the tubing and flow cells have not changed, it is expected that the physical mixing volume will be unchanged. FIG. 7 shows that it is nearly constant at around 40 µl.

Example 3

Figure 8:
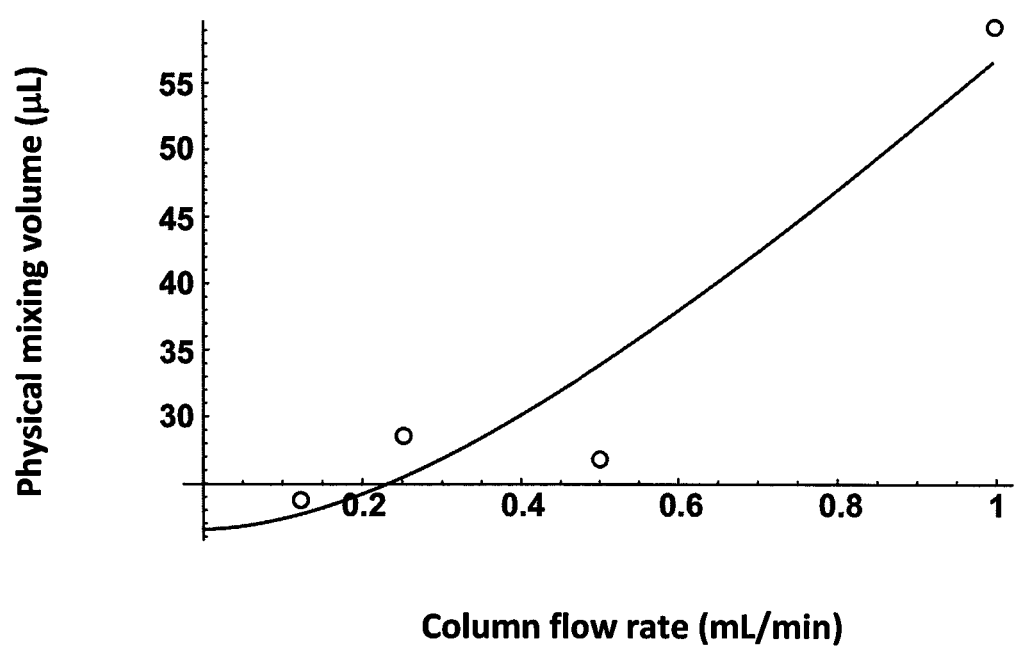
FIG. 8 is a graph showing the full width at half maximum (FWHM) in relation to the flow rate.

The next example measures the full width at half maximum (FWHM) of the LS peak as a function of the column flow rate. The purpose of this test is to quantify the increase in resolution demonstrated qualitatively in FIG. 3. The true width of the peak entering the light scattering instrument is not know a priori. It cannot be measured until after it has been corrupted by peak broadening, which occurs before or during its passage through the light scattering instrument. However, it is possible to measure the change in peak width as a function of dilution. Then, extrapolation to infinite dilution may be used to determine the true underlying peak width. The measured FWHM may be no narrower than 10 µl, since that is the size of the injection volume. However, since there is some broadening in the injector and in the tubing leading up to the dilution union, it was expected to be broader. The data is shown in FIG. 8. Superimposed on the data is an extrapolation to infinite dilution. The limiting peak width was approximately 22 µl, and the undiluted peak was around 56 µl. The conclusion is that the peak width for these very narrow peaks is dominated by mixing of the sample after the column but before the measurement. This is evidenced by an initial injection of 10 µl that, after passing through the tubing and the inline filter, was 22 µl wide when it arrived at the detection instrument. The difference between the true width of 24 µl and the measured width of 56 µl represents resolution that is lost due to mixing in the tubing and the flow cell. This demonstrates that the resolution can be recovered with the application of the dilution flow.

Without further elaboration, it is believed that one skilled in the art can use the preceding description to utilize the present disclosure to its fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles of the disclosure described herein. In other words, various modifications and improvements of the embodiments specifically disclosed in the description above are within the scope of the appended claims. The scope of the invention is, therefore, defined by the following claims.

The invention claimed is:

1. A method to minimize interdetector band broadening and narrow peak breadth of a chromatographic elution of a sample, the method consisting essentially of the steps of
   A. providing a column flow;
   B. providing a dilution flow;
   C. introducing an unfractionated sample into said column flow;
   D. passing said column flow borne unfractionated sample through a fractionation means, causing thereby a fractionated sample to elute from said fractionation means;
   E. mixing said column flow eluting from said fractionation means with said dilution flow, creating, thereby, a diluted, fractionated sample;
   F. passing, by interconnecting, tubing said diluted, fractionated sample to one or more analysis instruments connected in series by tubing; and
   G. analyzing said diluted, fractionated sample with said one or more analysis instruments.

2. The method of claim 1, wherein said column flow comprises a first solvent.

3. The method of claim 2, wherein said dilution flow comprises a second solvent.

4. The method of claim 3, wherein said first solvent and said second solvent are the same.

5. The method of claim 3, wherein said first solvent and said second solvent are different.

6. The method of claim 1, wherein said at least one analysis instrument comprises an instrument selected from the group consisting of a light scattering detector, a refractive index detector, an ultraviolet absorption detector, and combinations thereof.

7. The method of claim 1, wherein said fractionation means is configured to perform high performance liquid chromatography.

8. The method of claim 1, wherein said fractionation means performs chromatography techniques selected from the group consisting of ion exchange chromatography, size exclusion chromatography, affinity chromatography, gas-liquid chromatography, gas chromatography, and combinations thereof.

9. The method of claim 1, wherein said column flow is diluted by said dilution flow in a ratio ranging from 1:1 (1 part column flow to 1 part dilution flow 1) to 1:10 (1 part column flow to 10 parts dilution flow 1).

10. The method of claim 1 further comprising the step of filtering said diluted, fractionated sample prior to analysis by said one or more analysis instruments.

11. The method of claim 1 further comprising the step of filtering said unfractionated sample bearing column flow prior to said passage through said separation means.

12. The method of claim 1 further comprising the step of filtering said dilution flow prior to mixing with said column flow.

13. The method of claim 1 wherein said column flow and said dilution flow are mixed at a T-union.

14. The method of claim 13 wherein said mixing is continued in a downstream filter prior to analysis by said one or more analysis instruments.

* * * * *